(12) United States Patent
Riedel et al.

(10) Patent No.: US 10,814,070 B2
(45) Date of Patent: Oct. 27, 2020

(54) NEEDLE SHIELD REMOVER

(71) Applicant: SANOFI-AVENTIS DEUTSCHLAND GMBH, Frankfurt am Main (DE)

(72) Inventors: Stephan Riedel, Frankfurt am Main (DE); Uwe Dasbach, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 1143 days.

(21) Appl. No.: 14/905,477

(22) PCT Filed: Jul. 17, 2014

(86) PCT No.: PCT/EP2014/065418
§ 371 (c)(1),
(2) Date: Jan. 15, 2016

(87) PCT Pub. No.: WO2015/007857
PCT Pub. Date: Jan. 22, 2015

(65) Prior Publication Data
US 2016/0175539 A1 Jun. 23, 2016

(30) Foreign Application Priority Data
Jul. 18, 2013 (EP) .................................... 13176961

(51) Int. Cl.
*A61M 5/32* (2006.01)
(52) U.S. Cl.
CPC ........ *A61M 5/3204* (2013.01); *A61M 5/3202* (2013.01)

(58) Field of Classification Search
CPC ........ A61M 5/3204; A61M 2005/3217; A61M 5/3213; A61M 2005/3215; A61M 5/3269;
(Continued)

(56) References Cited

U.S. PATENT DOCUMENTS 5,279,591 A * 1/1994 Simon ................. A61M 5/3243
604/192
7,771,397 B1 8/2010 Olson
(Continued)

FOREIGN PATENT DOCUMENTS

WO WO2012/073040 6/2012
WO WO2013/058697 4/2013

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Lauren P Farrar
*Assistant Examiner* — Laura C Schell
(74) *Attorney, Agent, or Firm* — Fish & Richardson P.C.

(57) ABSTRACT

Described is a needle shield remover (6) comprising a needle cap (5), a carrier sheath (6.2) axially slidably disposed in the needle cap (5) and adapted to engage a needle shield (4) disposed on a needle (3), and a grip (6.1) transversely slidably disposed in the needle cap (5) and adapted to engage the carrier sheath (6.2) to displace the carrier sheath (6.2) and the needle shield (4) axially relative to the needle cap (5).

18 Claims, 5 Drawing Sheets

(58) Field of Classification Search
CPC ............ A61M 5/3202; A61M 5/3205–5/3219;
A61M 2005/312; A61M 2005/3118;
A61M 5/002–2005/005; A61M 5/1626;
A61M 5/1785; A61M 2005/3107; A61M
5/3243–5/3276
See application file for complete search history.

(56) References Cited

U.S. PATENT DOCUMENTS

| | | | |
|---|---|---|---|
| 2006/0089599 A1* | 4/2006 | Lynn .................. | A61M 5/3213 |
| | | | 604/111 |
| 2010/0286620 A1 | 11/2010 | Edginton et al. | |
| 2012/0186075 A1* | 7/2012 | Edginton ............ | A61M 5/2033 |
| | | | 29/700 |
| 2013/0253444 A1* | 9/2013 | Liversidge ............ | A61M 5/326 |
| | | | 604/263 |

OTHER PUBLICATIONS

International Preliminary Report on Patentability in Application No. PCT/EP2014/065418, dated Jan. 19, 2016.
International Search Report and Written Opinion in Application No. PCT/EP2014/065418, dated Nov. 4, 2014, 9 pages.

* cited by examiner

NEEDLE SHIELD REMOVER

CROSS-REFERENCE TO RELATED APPLICATIONS

This application is a U.S. national stage application under 35 USC § 371 of International Application No. PCT/EP2014/065418, filed on Jul. 17, 2014, which claims priority to European Patent Application No. 13176961.4, filed on Jul. 18, 2013, the entire contents of which are incorporated herein by reference.

TECHNICAL FIELD

The invention relates to a needle shield remover for removing a needle shield from a needle of a medicament container, and to a medicament delivery device comprising a medicament container having a needle with a needle shield.

BACKGROUND OF THE INVENTION

Many conventional medicament delivery devices, such as auto-injectors or medicament containers, have been developed for self-administration of a medicament. Such devices comprise a needle to ease the self-administration of the medicament. In order to maintain sterility of the needle sterile, the needle is typically covered with a needle shield made of a flexible material such as rubber.

To protect the needle from damage (e.g., bending) and to protect people from needlestick injuries, the needle shield can be encased by a protective needle cap made of a material that is more rigid than the material of the needle shield, as for example a plastic needle cap.

Although the conventional needle cap helps in preventing damage to the needle and needlestick injury, removal of the needle shield from the needle may require certain dexterity and force which some patients and/or caregivers do not possess. Thus, there is a need for a mechanism to provide easy, reliable and safe removal of the needle shield.

WO 2012/073040 A1 describes a safety device for shielding a medical needle having a sharp tip that includes a needle mount which is adapted directly or indirectly to support the needle.

SUMMARY OF THE INVENTION

It is an object of the present invention to provide a needle shield remover which supports an easy, reliable and safe removal of a needle shield from a medicament container. Further it is an object of the present invention to provide a medicament delivery device with an improved needle shield remover.

In an exemplary embodiment, a needle shield remover according to the present invention comprises a needle cap, a carrier sheath axially slidably disposed in the needle cap and adapted to engage a needle shield disposed on a needle, and a grip transversely slidably disposed in the needle cap and adapted to engage the carrier sheath along an abutting surface angled relative to a central axis of the needle cap to displace the carrier sheath and the needle shield axially relative to the needle cap.

In an exemplary embodiment, the needle cap includes one or more holes adapted to receive one or more grip handles disposed on the grip. The grip handles protrude radially from the one or more holes.

In an exemplary embodiment, the needle cap is made of a first material and the needle shield is made of a second material, wherein the first material has a higher durometer than the second material.

In an exemplary embodiment, the carrier sheath includes proximal ends adapted to engage the grip handles when the grip handles translate transversely relative to the needle cap. The proximal ends are angled relative to a central axis of the needle cap. The grip handles have inner surfaces adapted to engage the proximal ends and the inner surfaces are disposed at an angle relative to a central axis of the needle cap.

In an exemplary embodiment, the needle shield remove further includes one or more barbs adapted to engage the needle shield. The proximal ends are adapted to engage the one or more barbs.

In an exemplary embodiment, the needle shield remove further includes a cone adapted to engage the needle shield. The proximal ends are adapted to engage a proximal end of the cone.

In an exemplary embodiment, the grip is a partial ring.

In an exemplary embodiment, the grip is made of a deformable material. The deformable material has shape memory.

In an exemplary embodiment, a medicament delivery device according to the present invention comprises a medicament container, a needle coupled to the medicament container, a needle shield coupled to the needle, and a needle shield remover according to any of the exemplary embodiments of the present invention.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
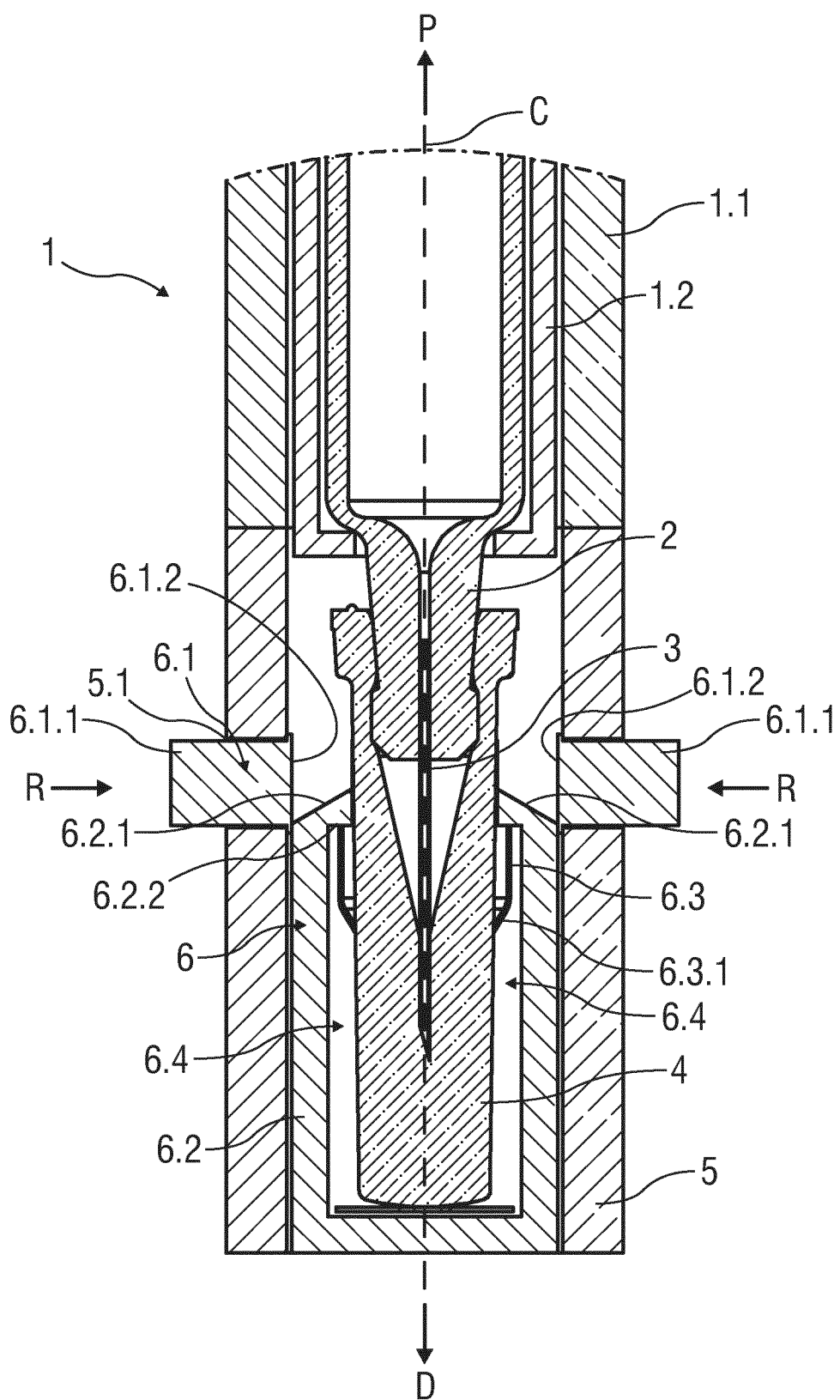
FIG. 1A is a partial longitudinal section of an exemplary embodiment of a medicament delivery device with an exemplary embodiment of a needle shield remover according to the present invention.

FIG. 1A shows a medicament delivery device 1 comprising a housing 1.1 and a medicament container carrier 1.2. In an exemplary embodiment, the medicament container carrier 1.2 is adapted to hold and encase a medicament container 2 with a pre-mounted needle 3. The medicament container 2 may be a pre-filled medicament container 2 (e.g., a syringe) pre-filled with a medicament. The needle 3 is substantially aligned with a central axis C of the medicament delivery device 1. In another exemplary embodiment, the medicament container 2 may be a standalone medicament container 2 which is not inside a medicament delivery device 1. In another exemplary embodiment, the medicament container 2 may be an ampoule or a cartridge adapted to engage a removable needle assembly.

In an exemplary embodiment, the needle 3 is covered by a removable needle shield 4 that maintains the sterile condition of the needle 3 and of the content of the medicament container 2. The needle shield 4 is made of a material such as rubber. It may be fitted to a distal part (e.g., a neck portion) of the medicament container 2 by friction.

To remove the needle shield 4 a removal force is required that overcomes static friction between the material of the needle shield 4, for example rubber, and the material of the medicament container, for example thermoplastic or glass. Because of differences between the materials and their properties, and effects on such properties due to, for example, age, temperature and humidity, the removal force can vary. Sometimes, the removal force can rise up to 35 Newton.

In an exemplary embodiment, a needle cap 5 may encase the needle shield 4 and optionally a distal part of the medicament container 2. In an exemplary embodiment, the needle cap 5 is formed from a rigid material having a higher durometer than the needle shield. In an exemplary embodiment, the needle cap 5 may be formed as a cylinder with e.g., a circular or polygonal cross-section, and aligned with the central axis C with an open distal and proximal ends.

In an exemplary embodiment, a needle shield remover 6 having a grip 6.1 and a carrier sheath 6.2. In an exemplary embodiment, the grip 6.1 comprises at least two grip handles 6.1.1 radially protruding through openings 5.1 in a side wall of the needle cap 5. As shown in the exemplary embodiment of FIG. 1A, the at least two grip handles 6.1.1 are arranged opposite each other and each of them is pin-shaped. In another exemplary embodiment, the grip handles 6.1.1 may be formed as resilient beams disposed in slots formed in the needle cap 5.

In an exemplary embodiment, the grip handles 6.1.1 comprise an inner surface 6.1.2 which may have a retaining element (e.g., a flange) which has a larger cross-section than the openings 5.1. The retaining element may ensure that the grip handles 6.1.1 do not fall radially out of the openings 5.1. The grip handles 6.1.1 are slideable within the openings 5.1 in a radial direction R towards the central axis C. The grip handles 6.1.1 may further slide in an opposite radial direction (away from the central axis C).

In particular, the grip 6.1 is transversely slidably disposed in the needle cap 5 and adapted to engage the carrier sheath 6.2 along an abutting surface angled relative to a central axis C of the needle cap 5 to displace the carrier sheath 6.2 and the needle shield 4 axially relative to the needle cap 5.

In an exemplary embodiment, the carrier sheath 6.2 is arranged concentrically between the needle cap 5 and the needle shield 4. The carrier sheath 6.2 may be formed as a cylinder with a closed distal end and an opened proximal end with an angled proximal edge 6.2.1. In an exemplary embodiment, the distal end of the carrier sheath 6.2 may be aligned with the distal end of the needle cap 5, such that the carrier sheath 6.2 does not protrude distally beyond the distal end of the needle cap 5.

In an exemplary embodiment, the angled proximal edge 6.2.1 is formed such that the outer perimeter of the carrier sheath 6.2 is reduced in the proximal direction P. In particular, the proximal angled proximal edge 6.2.1 may have a circumferential inclination of an angle in the range from 35° to 45° relative to a transverse axis of the needle shield 4. The angled proximal edge 6.2.1 provides an opening that receives the needle shield 4 and is extended radially inwards to form an inside edge 6.2.2 that engages the outer surface of the needle shield 4.

When assembled to the needle shield 4, the angled proximal edges 6.2.1 are disposed adjacent to the openings 5.1 of the needle cap 5. Hence, the inner surface of the grip handles 6.1.1 directed inwards may abut the angled proximal edge 6.2.1 of the carrier sheath 6.2.

In an exemplary embodiment, a portion of the carrier sheath 6.2 distal of the angled proximal edge 6.2.1 may have a larger inner diameter than the outer diameter of the needle shield 4 so that a gap 6.4 is formed between the needle shield 4 and the carrier sheath 6.2. Due to the gap 6.4 between the needle shield 4 and the needle cap 5, at least in the area of the grip handles 6.1.1 at the inside edge 6.2.2 and thus opposing the angled proximal edge 6.2.1 of the carrier sheath 6.2 a proximal recess is formed.

In an exemplary embodiment, one or more barbs 6.3 are coupled to the inside edge 6.2.2. As an example, it is possible to attach barbs 6.3 during injection molding when manufacturing a carrier sheath 6.2 made of plastics. It is also possible to releasably attach barbs 6.3, for example by leading each barb 6.3 into a blind hole that was introduced into the inside edge 6.2.2 essentially in parallel to the central axis C. Distal endings 6.3.1 of the barbs 6.3 are bent towards the central axis C. Thus, the bent distal endings 6.3.1 engage the needle shield 4 when the carrier sheath 6.2 is moved in the distal direction D.

To remove the needle shield 4 from the needle 3, the grip handles 6.1.1 are pressed in the radial direction R towards the central axis C. As the grip handles 6.1.1 translate radially they engage the angled proximal edge 6.2.1 of the carrier sheath 6.2. Applying radial force on the angled proximal edge 6.2.1 causes the carrier sheath 6.2 to translate distally relative to the needle cap 5. As the carrier sheath 6.2 translates distally, the bent endings 6.3.1 engage the needle shield 4 and push in the distal direction D. The needle shield 4 is at least partially removed from the needle 3, and the needle cap 5 can be pulled away from the needle 3 to expose the needle 4 with significantly less force than pulling the needle shield 4 alone.

Figure 1B:
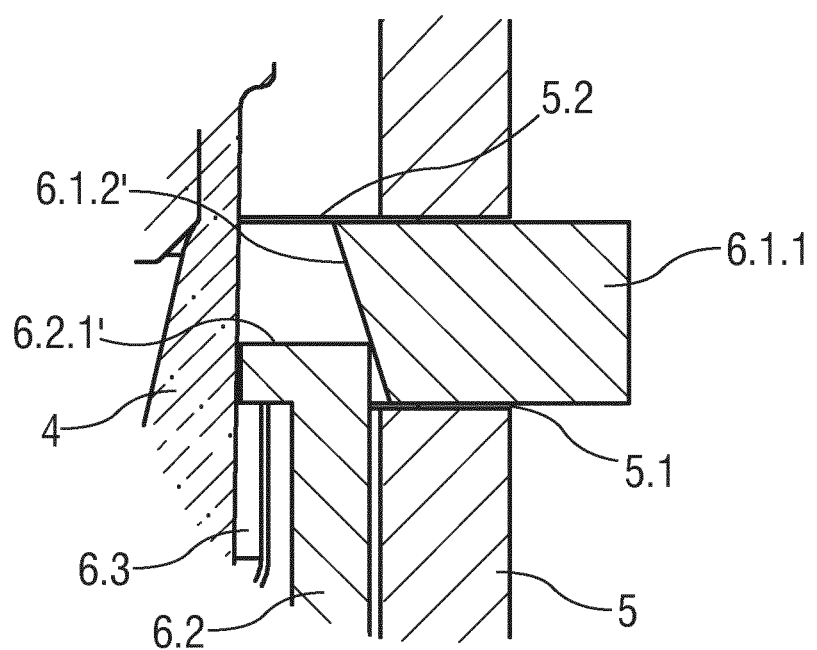
FIG. 1B is a partial longitudinal section of a medicament delivery device with a further exemplary embodiment of a needle shield remover according to the present invention.

FIG. 1B shows a partial longitudinal section of a further exemplary embodiment of a needle shield remover 6 according to the present invention. In this exemplary embodiment, a proximal end 6.2.1' of the carrier sheath 6.2 is inwardly bent approximately perpendicular to the central axis C to form the inside edge 6.2.2 for holding the barbs 6.3, and an inner surface 6.1.2' of the grip handles 6.1.1 is angled or sloped by an angle of 35° to 45° relative to the central axis C. In operation, the grip handles 6.1.1 are pressed in the radial direction R towards the central axis C. As the grip handles 6.1.1 translate radially, the inner surface 6.1.2' engages the proximal end 6.2.1' of the carrier sheath 6.2. Applying radial force on the proximal end 6.2.1' causes the carrier sheath 6.2 to translate distally relative to the needle cap 5. As the carrier sheath 6.2 translates distally, the bent endings 6.3.1 engage the needle shield 4 and push in the distal direction D. The needle shield 4 is at least partially removed from the needle 3, and the needle cap 5 can be pulled away from the needle 3 to expose the needle 4.

Figure 1C:
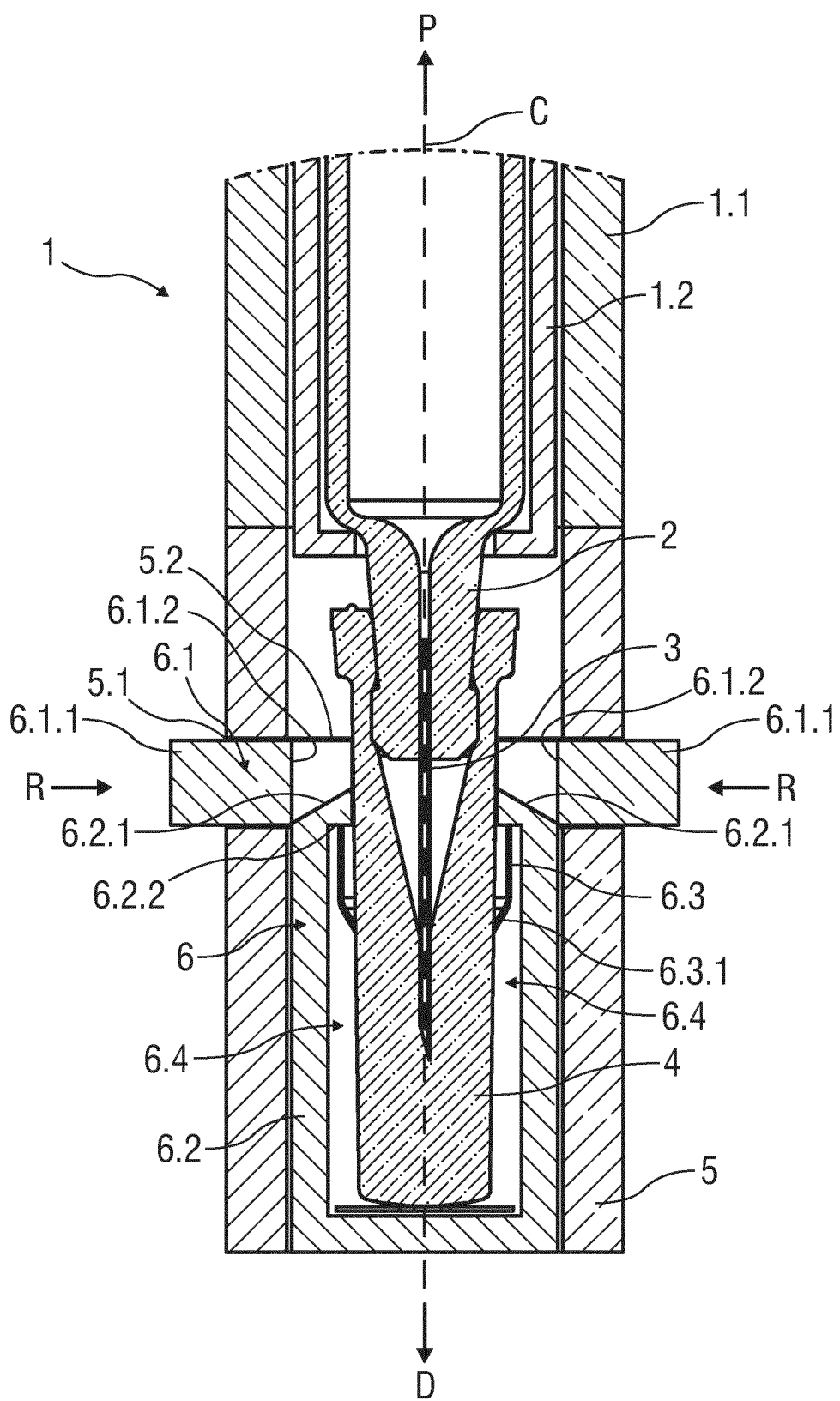
FIG. 1C is a partial longitudinal section of a medicament delivery device with a further exemplary embodiment of a needle shield remover according to the present invention.
Figure 2A:
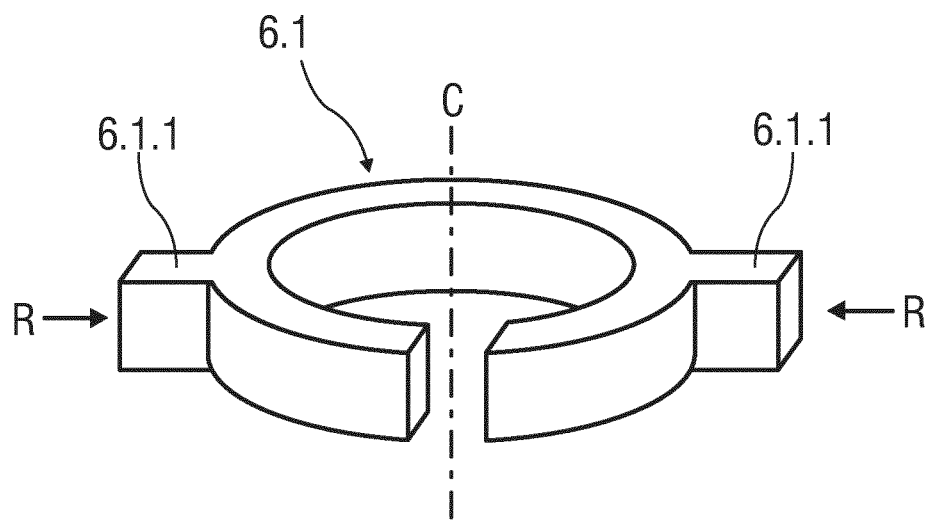
FIG. 2A is a longitudinal section of an exemplary embodiment of a grip for a needle shield remover according to the present invention.

FIGS. 1C and 2A show an exemplary embodiment a grip 6.1 in more detail, wherein the grip 6.1 is formed as a slotted ring. Two radially protruding grip handles 6.1.1 are aligned with a diameter through the ring. It is also possible to have a plurality of more than two radially protruding grip handles 6.1.1, e.g. arranged rotationally symmetric around the central axis C through the centre of the ring of the grip 6.1. Furthermore, it is possible, to arrange a single protruding grip handle 6.1.1. The grip handles 6.1.1 of the ring radially protrude through the openings 5.1 in the side wall of the needle cap 5. The ring is arranged concentrically between a cylindrically formed needle cap 5 and the needle shield 4. In particular, outside the openings 5.1 the ring is arranged in a partly circumferential recess 5.2 in the wall of the needle cap 5.

In an exemplary embodiment for sliding the grip handles 6.1.1 in a radial direction R, the grip 6.1 may be formed as a slotted ring. In other words: The grip 6.1 may be open along its perimeter, with the opening arranged in a ring sector between grip handles 6.1.1. In particular, the grip 6.1 according to this embodiment provides a radial slot through its ring shaped perimeter. In an exemplary embodiment, the slot is arranged symmetrically between two grip handles 6.1.1.

In yet a further embodiment, the grip 6.1 is made of a compressible or deformable material in order to allow the grip handles 6.1.1 to slide in a radial direction R relative to the needle cap 5.

When the grip handles 6.1.1 are pressed in the radial direction R towards the central axis C, the radial slot is reduced or closed. Depending on the material of the grip 6.1, the slotted ring may act as a spring with respect to a load applied in the radial direction R onto the grip handles 6.1.1. To those skilled in the art, many materials are known that provide sufficient elasticity and rigidity such as thermoplastics or steel.

The inner surface 6.1.2 of the grip 6.1 is adapted to abut the engage proximal edge/ends 6.2.1. When the grip handles 6.1.1 are pressed toward the central axis C, the angled proximal edge 6.2.1 and thus the carrier sheath 6.2 are driven in the distal direction D so that the rigid barbs 6.3 either prick into or fit tightly to the needle shield 4. The needle shield 4 is forced and moved in the distal direction D relative to the needle cap 5 via the fitted or partly inserted rigid barbs 6.3, so that the removal of the needle shield 4 can be accomplished or supported.

Figure 2B:
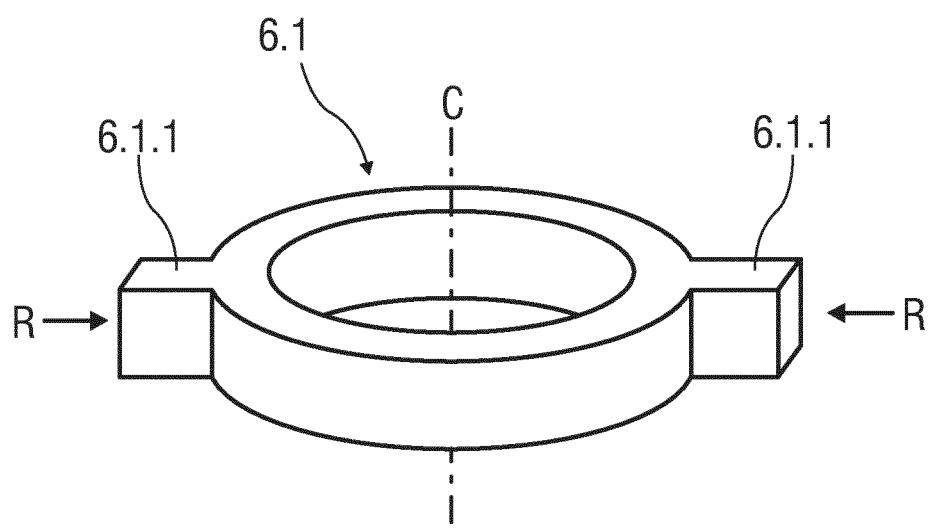
FIG. 2B is a longitudinal section of a further exemplary embodiment of a grip for a needle shield remover according to the present invention and FIG. 3 is a longitudinal section of a rigid axial connector according to an exemplary embodiment of a needle shield remover according to the present invention.

FIG. 2B shows a further exemplary embodiment of a grip 6.1, wherein the grip 6.1 is formed as a closed ring made of a deformable material. When the grip handles 6.1.1 are compressed towards the central axis C, the closed ring deforms. To those skilled in the art, various materials for a grip 6.1 according to this embodiment are known that provide sufficient elasticity such that the grip 6.1 acts as a spring along a radial direction R.

Figure 3:
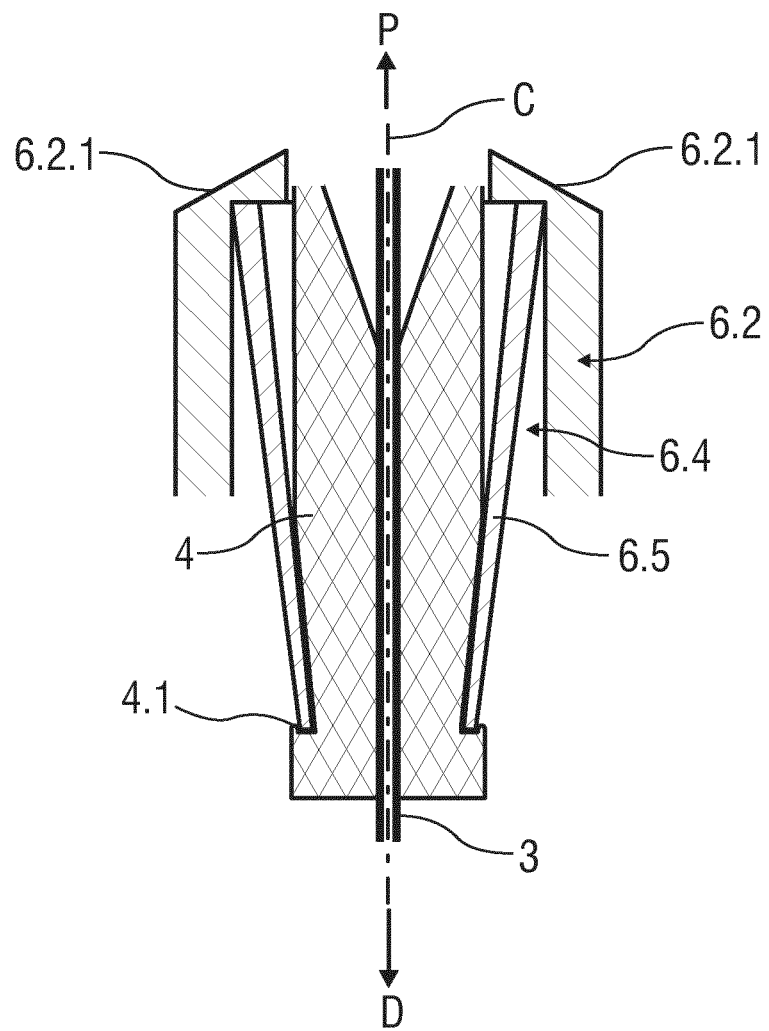

FIG. 3 shows a further embodiment of a carrier sheath 6.2 formed as a cone 6.5 with a reduced inner diameter on its distal end instead of barbs 6.3. This reduced inner diameter is chosen slightly smaller than the outer diameter of the needle shield 4 such that it tightly fits the needle shield 4. The inner diameter of the cone 6.5 on the proximal end is chosen wider than the perimeter of the needle shield 4. The outer diameter of the proximal end of the cone 6.3 is chosen such that the proximal end of the cone 6.3 abuts the distal surface of the angled proximal edge 6.2.1.

Due to its widened proximal end, the cone 6.5 can be slid easily over the needle shield 4 in the proximal direction P. On its distal end the inner diameter of the cone 6.3 slightly constricts the needle shield 4, causing the material of the needle shield 4 to bulge distally of the distal ending of the cone 6.3. The bulge 4.1 prevents a sliding of the cone 6.5 over the needle shield 4 in a distal direction D. Therefore, the cone 6.5 may transform a force substantially directed into the distal direction D from the angled proximal edge 6.2.1 onto the needle shield 4 that supports the removal of the needle shield 4 from the medicament container 2 and the needle 3.

The cone 6.5 may be inexpensive to manufacture and particularly easy to assemble with the needle cap 5, the needle shield 4 and the grip 6.1. It can be made from a variety of materials known to those skilled in the art such as thermoplastics or metal.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle shield remover, comprising:
   a needle cap;
   a carrier sheath axially slidably disposed in the needle cap and adapted to engage a needle shield disposed on a needle; and
   a grip disposed in the needle cap, the grip configured to slide in a perpendicular direction relative to a longitudinal axis of the needle cap and to engage the carrier sheath along an abutting surface of the grip or carrier sheath, angled relative to the longitudinal axis of the needle cap to displace the carrier sheath and the needle shield axially relative to the needle cap.

2. The needle shield remover according to claim 1, wherein the needle cap includes one or more holes adapted to receive one or more grip handles disposed on the grip.

3. The needle shield remover according to claim 2, wherein each grip handle of the one or more grip handles protrudes from a corresponding hole of the one or more holes.

4. The needle shield remover according to claim 2, wherein the carrier sheath includes a plurality of proximal ends adapted to engage the one or more grip handles when the one or more grip handles translate transversely relative to the needle cap.

5. The needle shield remover according to claim 4, wherein the plurality of proximal ends are angled relative to the longitudinal axis of the needle cap.

6. The needle shield remover according to claim 4, wherein each grip handle of the one or more grip handles has a respective inner surface adapted to engage a respective proximal end of the plurality of proximal ends and each respective inner surface is disposed at an angle relative to the longitudinal axis of the needle cap.

7. The needle shield remover according to claim 4, wherein each respective proximal end of the plurality of proximal ends is adapted to engage a respective barb of one or more barbs that are adapted to engage the needle shield.

8. The needle shield remover according to claim 4, wherein the plurality of proximal ends are adapted to engage a proximal end of a cone that is adapted to engage the needle shield.

9. The needle shield remover according to claim 1, wherein the needle cap is made of a first material and the needle shield is made of a second material, wherein the first material has a higher durometer than the second material.

10. The needle shield remover according to claim 1, further including one or more barbs adapted to engage the needle shield.

11. The needle shield remover according to claim 1, further including a cone adapted to engage the needle shield.

12. The needle shield remover according to claim 1, wherein the grip is a partial ring.

13. The needle shield remover according to claim 1, wherein the grip is made of a deformable material.

14. The needle shield remover according to claim 13, wherein the deformable material has shape memory.

15. The needle shield remover according to claim 1, wherein the grip comprises two grip handles disposed on opposite sides of the grip.

16. A medicament delivery device, comprising:
a medicament container;
a needle coupled to the medicament container;
a needle shield coupled to the needle; and
a needle shield remover comprising:
  a needle cap,
  a carrier sheath axially slidably disposed in the needle cap and adapted to engage the needle shield disposed on the needle, and
  a grip disposed in the needle cap, the grip configured to slide in a perpendicular direction relative to a longitudinal axis of the needle cap and to engage the carrier sheath along an abutting surface angled relative to the longitudinal axis of the needle cap to displace the carrier sheath and the needle shield axially relative to the needle cap.

17. A method comprising:
pressing grip handles in a radial direction towards a longitudinal axis of a needle cap;
engaging the grip handles with angled proximal edges of a carrier sheath;
applying a radial force on the angled proximal edges by the grip handles, the radial force translating the carrier sheath distally relative to the needle cap;
the carrier sheath engaging a needle shield and translating the needle shield distally, the needle shield being at least partially removed from a needle; and
removing the needle cap and exposing the needle.

18. The method according to claim 17, wherein pressing the grip handles in the radial direction towards the longitudinal axis of the needle cap slides the grip handles in a direction perpendicular to the longitudinal axis of the needle cap.

* * * * *